(12) United States Patent
Pelletier

(10) Patent No.: US 8,047,707 B2
(45) Date of Patent: Nov. 1, 2011

(54) PASSIVE THERMAL IMAGE GLASS BREAKAGE DETECTOR

(75) Inventor: Kevin M. Pelletier, Rocklin, CA (US)

(73) Assignee: Honeywell International Inc., Morristown, NJ (US)

(*) Notice: Subject to any disclaimer, the term of this patent is extended or adjusted under 35 U.S.C. 154(b) by 83 days.

(21) Appl. No.: 12/617,455

(22) Filed: Nov. 12, 2009

(65) Prior Publication Data

US 2010/0052905 A1 Mar. 4, 2010

Related U.S. Application Data

(62) Division of application No. 11/961,217, filed on Dec. 20, 2007, now Pat. No. 7,637,652.

(51) Int. Cl.
*G01N 25/72* (2006.01)
*G01J 5/00* (2006.01)

(52) U.S. Cl. ............... 374/4; 374/121; 374/45

(58) Field of Classification Search .............. 374/4, 121, 374/45
See application file for complete search history.

(56) References Cited

U.S. PATENT DOCUMENTS

| 7,422,365 B2* | 9/2008 | Chamberlain et al. ........ 374/120 |
| 2004/0076216 A1* | 4/2004 | Chamberlain et al. ......... 374/57 |
| 2005/0207468 A1* | 9/2005 | McCullough et al. ............ 374/5 |

\* cited by examiner

*Primary Examiner* — Lisa Caputo
*Assistant Examiner* — Mirellys Jagan
(74) *Attorney, Agent, or Firm* — Husch Blackwell

(57) ABSTRACT

A system and method for detecting glass breakage using thermal imaging is provided. The system includes an infrared image detector for acquiring an infrared image of a monitored area, and a signal processor for processing the acquired images to determine removal of a glass door or window based on a comparison of the thermal signature of the acquired image against the thermal signature of a reference image. Specifically, signal processor subtracts the reference image data from the acquired image data, which results in a substantially uniform image when the acquired image matches the reference image. On the other hand, the image resulting from the subtraction exhibits significant non-uniformity when the acquired image does not match the reference image, as would be the case if the pane of glass of a door or window were broken, removed or opened.

8 Claims, 4 Drawing Sheets

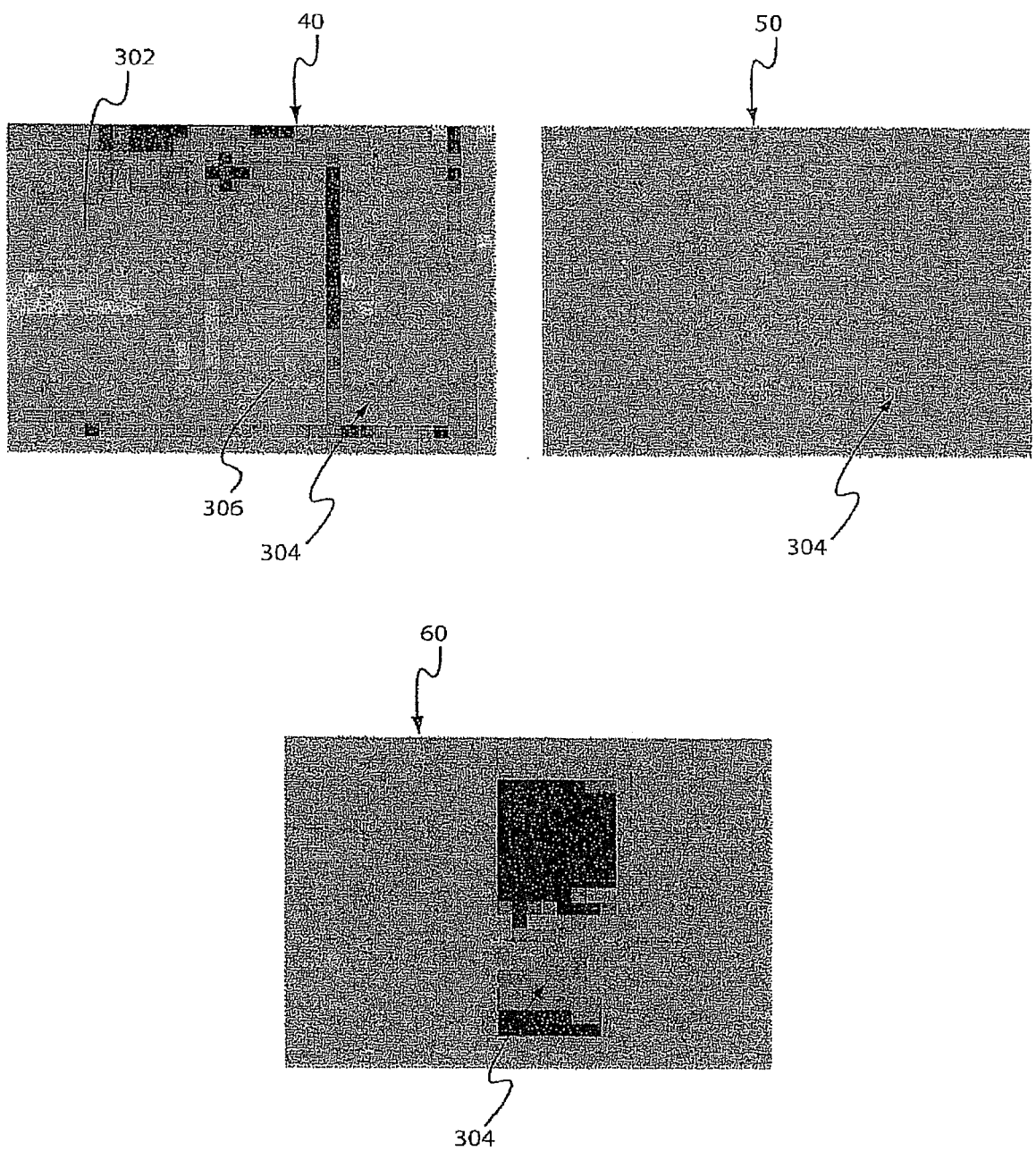

PASSIVE THERMAL IMAGE GLASS BREAKAGE DETECTOR

CROSS-REFERENCE TO RELATED APPLICATIONS

This application is a Divisional of and claims the benefit of the filing date of U.S. application Ser. No. 11/961,217 filed Dec. 20, 2007.

I. FIELD OF THE INVENTION

The present invention relates generally to security systems and more particularly to glass breakage detectors.

II. BACKGROUND OF THE DISCLOSURE

Current glass break technology utilizes either acoustic or shock sensing methods to determine the glass break event. The inherent weakness with both of these systems is they can be defeated with specific break methods. In one example, a center punch or torch can be used that will go undetected by prior art detection systems.

III. SUMMARY OF THE DISCLOSURE

An embodiment of the present invention utilizes an infrared image of a pane of glass to determine the presence of the glass, thus preventing any chance of defeat. A glass pane will have a fairly uniform temperature. The inside temperature of the glass will be different than the outside temperature. If the glass is broken/removed the IR scene will quickly change and no longer be uniform and/or thermally different presenting the data for an alarm event.

An embodiment of the present invention includes an image detector for acquiring thermal images of a monitored area including a glass portion. The image detector is a 2-dimensional microbolometer. However, other devices capable of sensing the desired portion of IR spectrum, such as pyroelectric sensor arrays and focal plane arrays, may be used as well. A signal processor generates a reference image from a thermal image of the monitored area, comparing acquired thermal images against the reference image. The reference image provides a baseline thermal signature of the monitored area when the glass portion is present. A memory unit stores the reference image and an optics assembly is additionally provided for forming an image of the monitored area onto the image detector.

Additionally depending on the algorithms utilized, the microprocessors etc., a 1D array of data ie. 20×20 pixel detector could just output a string of 400 data points. The algorithm just compares the 400 data points for changes.

Optionally, the signal processor generates a new reference image for replacing a previous reference image at predefined intervals. Moreover, the compared thermal image is determined as unchanged with respect to the reference image if differences between the thermal image and the reference image are within a predefined threshold, and determined as changed if differences between the thermal image and the reference image exceed the predefined threshold. A glass breakage alert is issued, i.e. generated and outputted, if the thermal image is determined to be changed.

In another embodiment, the glass breakage alert is issued only after acquiring thermal images determined to be changed over a preset interval of time, and not issue a glass breakage alert if a thermal image is acquired within the preset interval of time that is determined to be unchanged with respect to the reference image. The temperature of glass will change relatively slowly compared to a break or removal stimulus, thus gradual changes are easily ignored while sudden changes that may indicate glass breakage or opening of a glass window or door will register as a fault.

Additionally, a process for detecting glass breakage in accordance with the present invention includes the steps of acquiring thermal images of a monitored area including a glass portion; generating a reference image from a thermal image of the monitored area; comparing subsequently acquired thermal images against the reference image; and generating a glass breakage alert when the comparison indicates a change in thermal signature with respect to the reference image.

IV. BRIEF DESCRIPTION OF THE DRAWINGS

These and other features, aspects, and advantages of the present invention will become better understood with regard to the following description, appended claims, and accompanying drawings wherein:

FIG. 3b illustrates a series of low resolution infrared images acquired by embodiments of the present invention.

V. DETAILED DESCRIPTION OF DISCLOSURE

Figure 1:
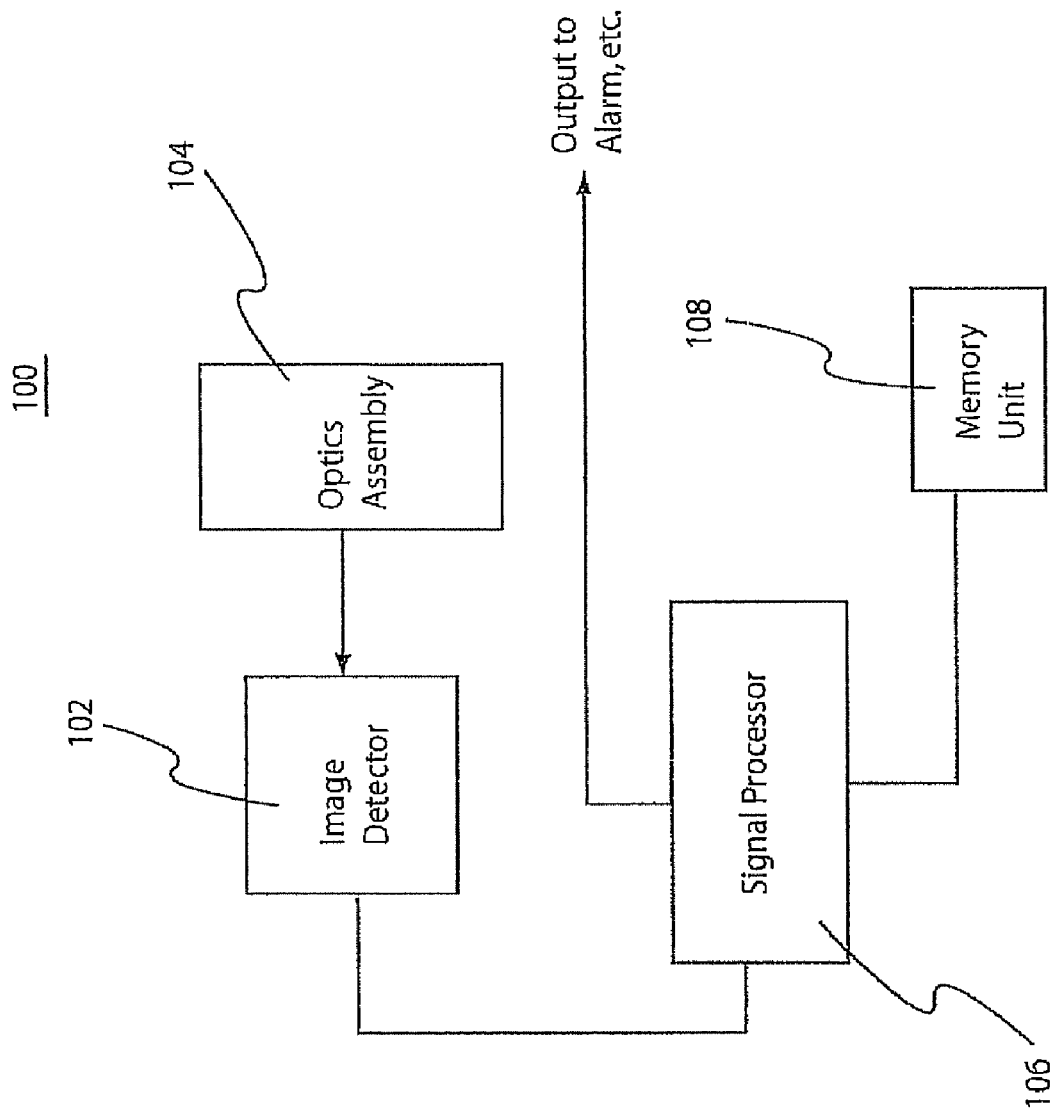
FIG. 1 illustrates a block representation of an embodiment of the present invention.

Turning now to FIG. 1, a block representation of an embodiment of a glass breakage detector system in accordance with the present invention. The glass breakage detector system 100 includes an infrared image detector 102, such as a focal plane array (FPA) or a 2-dimensional microbolometer array, with wavelength sensitivity above 5 µm. Hereinafter, the present invention will be described using a microbolometer array, however an FPA or other sensor capable of detecting the desired segment of electromagnetic spectrum can be substituted. In addition, an optics assembly 104 is provided for focusing a target area to be monitored onto the image detector 102.

A signal processor 106 receives image signals from the image detector 102 and normalizes the pixels of the image with a predefined normalization function. The normalization is performed by using a reference image of the target area stored in a memory unit 108 to subtract pixel data from the received image. The reference image and the received image are compared and pixel values of the reference image are subtracted from corresponding pixel values of the received image. Subtraction of the reference image from the received image will produce a generally uniform and neutral colored normalized image when the two images are substantially similar. However, if the thermal signature of the received image is significantly altered from the reference image, as would be the case if the glass door is broken, the resulting normalized image lacks uniformity.

Alternatively, the reference image and the received image can be compared. If the two images are identical, or nearly so with in a predefined threshold, the signal processor 106 determines that the glass is intact. However, if the comparison results in significant differences, the signal processor 106 determines that the glass has been broken and transmit an alarm signal to an output device such as a siren.

The data provided from the detector 202 is used to determine the thermal, or infrared, signature of existing glass. Algorithms for ignoring low frequency changes in the infrared scene as the glass changes temperature can be incorporated into the present invention. One such algorithm requires that changes in thermal signature surpass a preset threshold within a specific time interval. Thus, slow temperature changes of the glass caused by temperature fluctuations on either side of the glass would not trigger a glass breakage alert, while sudden temperature changes resulting from the glass being broken, opened or removed would trigger an alert. In this embodiment, the reference image may be taken at preset intervals so that the reference image incorporates the gradual thermal changes.

Furthermore in one embodiment, the detection system 100 can be configured to differentiate between a foreign object between the glass and the sensor versus glass removal, by providing a time interval in which the pixels must return to the expected values in order to avoid issuance of a glass breakage alert by the detector. Thus, for example, the detector of the present invention may require that the pixels of the acquired images return to expected values within a time interval of several seconds. In this way, an alert is not triggered by a person walking between the detector and the glass portion.

Figure 2:
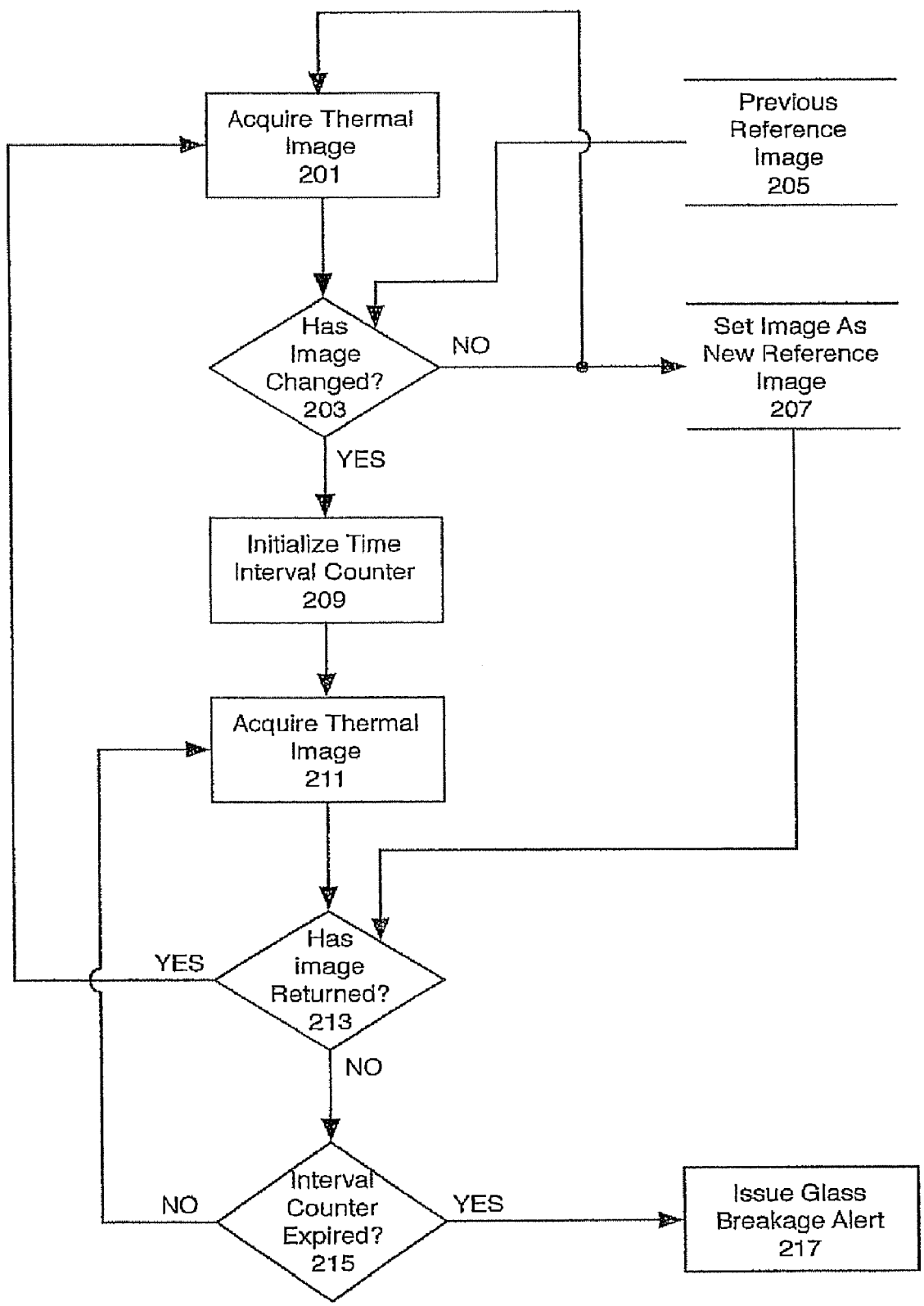
FIG. 2 provides a flowchart illustrating the steps for detecting glass breakage in accordance with an embodiment of the present invention.

FIG. 2 provides a flowchart illustrating the steps performed by an embodiment of the present invention. The detector begins glass breakage detection in step 201 by acquiring a thermal image. The acquired thermal image is compared with a reference image 205 stored in a memory unit in step 203. If a reference image 205 is not present, as would be the case during initial operation of the detector after installation, then the acquired image is set as the new reference image 207 and the process returns to step 201 to acquire a new thermal image. Otherwise, the outcome of the comparison step 203 determines if the thermal image has changed beyond a preset threshold.

If the acquired thermal image has not changed with respect to the previous reference image 205 beyond the preset threshold, the acquired thermal image is set as the new reference image 207, replacing the previous reference image 205. The process then returns to step 201, ready to acquire a new thermal image.

However, if the acquired thermal image has been determined to have changed beyond the preset threshold in step 203, the process continues to step 209. At step 209, an interval counter is initialized. The interval counter operates for a predetermined interval and is used to compensate for random movement between the detector and the monitored glass portion. With the counter initialized, the process proceeds to step 211 where a subsequent thermal image is acquired.

The subsequent thermal image acquired in step 211 is compare to the reference image 207. If this thermal image now matches the reference image 207, the process returns to step 201. On the other hand, if this thermal image does not match the reference image 207, the process proceeds to step 215, where the counter is checked to determine if the predefined amount of time has elapsed. If the predefined time interval has elapsed, then a glass breakage alert is issued in step 217. Otherwise, the process returns to step 211 and continues as described previously.

Figure 3A:
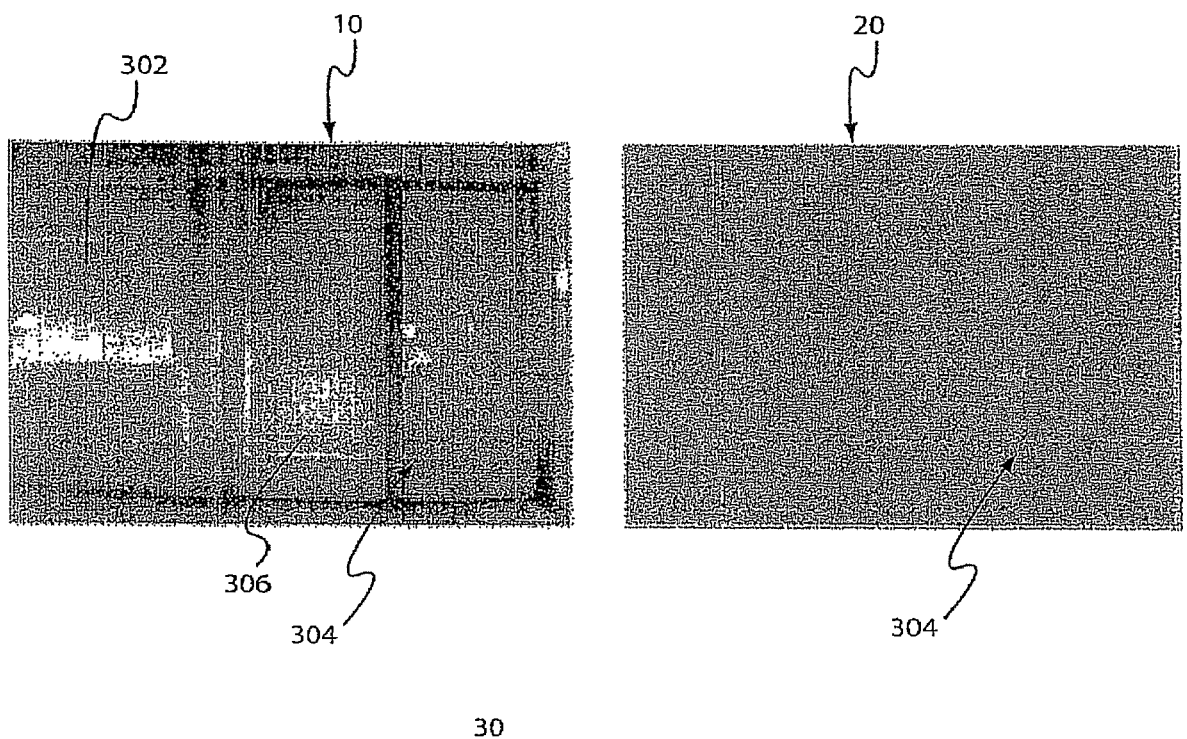
FIG. 3a illustrates a series of high resolution infrared images acquired by embodiments of the present invention.

Referring to FIG. 3, image 10 shows a high resolution infrared image of a section of wall 302 including door 304 with a substantial pane of glass 306. As can be seen from image 10, the glass door 304 is clearly discernable. Image 20 shows the same scene as in image 10, however the scene is normalized so that the pixels are essentially of uniform brightness when the glass door 304 is whole and closed. The normalization is performed so that a change in thermal energy can most readily be detected as shown in image 30. Normalization is performed by subtracting a reference image used as a baseline thermal signature of the monitored area from the acquired image data.

In image 30, the glass door 304 has been opened, or the glass 306 shattered, thus the infrared image sensor generates an image 30 that is easily distinguished from the normalized image 20. A processor can carry out the comparison of the normalized image 20 with image 30, and thus the glass breakage detection and alarm activation can be automatically performed without the aid of security personnel.

Regarding Images 40, 50 and 60, a low resolution infrared image is shown of the same scene in image 10 and correspond to images 10, 20 and 30, respectively. In the case of these images, a 32×32 pixel infrared array is used. As can be seen, even at this low resolution the open/broken glass 306 is clearly discernible in image 60.

The described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

What is claimed is:

1. A method for detecting glass breakage, said method comprising:
    acquiring thermal images of a monitored area including a glass portion;
    generating a reference image from a thermal image of said monitored area;
    comparing subsequently acquired thermal images against said reference image; and
    generating a glass breakage alert when said comparison indicates a change in thermal signature with respect to said reference image,
    wherein said compared thermal image is determined as unchanged with respect to said reference image if differences between said thermal image and said reference image are within a predefined threshold, and determined as changed if differences between said thermal image and said reference image exceed said predefined threshold.

2. The method as in claim 1, wherein said reference image provides a baseline thermal signature of said monitored area when said glass portion is present.

3. The method as in claim 1, wherein a new reference image is generated at predefined intervals, said new reference image replacing a previous reference image.

4. The method as in claim 1, wherein said glass breakage alert is generated only after acquiring thermal images determined to be changed over a preset interval of time, and not issuing a glass breakage alert if a thermal image is acquired within said preset interval of time that is to be determined unchanged with respect to said reference image.

5. A method for detecting glass breakage, said method comprising:
    acquiring thermal images of a monitored area including a glass portion;
    generating a reference image from a thermal image of said monitored area;
    comparing subsequently acquired thermal images against said reference image; and generating a glass breakage alert when said comparison indicates a change in thermal signature with respect to said reference image,
wherein said glass breakage alert is generated only after acquiring thermal images determined to be changed over a preset interval of time, and not issuing a glass breakage alert if a thermal image is acquired within said preset interval of time that is to be determined unchanged with respect to said reference image.

6. The method as in claim 5, wherein said reference image provides a baseline thermal signature of said monitored area when said glass portion is present.

7. The method as in claim 5, wherein a new reference image is generated at predefined intervals, said new reference image replacing a previous reference image.

8. The method as in claim 5, wherein said compared thermal image is determined as unchanged with respect to said reference image if differences between said thermal image and said reference image are within a predefined threshold, and determined as changed if differences between said thermal image and said reference image exceed said predefined threshold.

* * * * *